(12) United States Patent
Pirie-Shepherd et al.

(10) Patent No.: US 7,157,556 B1
(45) Date of Patent: Jan. 2, 2007

(54) DEGLYCOSYLATED KRINGLE 1-3 REGION FRAGMENTS OF PLASMINOGEN AND METHODS OF USE

(75) Inventors: Steven Pirie-Shepherd, Waltham, MA (US); M. Judah Folkman, Brookline, MA (US); Kim Lee Sim, Gaithersburg, MD (US); Nicholas MacDonald, Chevy Chase, MD (US); Hong LiAng, Gaithersburg, MD (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/502,176

(22) Filed: Feb. 10, 2000

Related U.S. Application Data

(60) Provisional application No. 60/119,562, filed on Feb. 10, 1999, provisional application No. 60/128,062, filed on Apr. 7, 1999.

(51) Int. Cl.
| | |
|---|---|
| C07K 1/00 | (2006.01) |
| C07K 14/00 | (2006.01) |
| C07K 17/00 | (2006.01) |
| C07K 16/00 | (2006.01) |
| A61K 35/14 | (2006.01) |
| A61K 38/16 | (2006.01) |
| A01N 61/00 | (2006.01) |
| C07H 21/02 | (2006.01) |

(52) U.S. Cl. .................. 530/350; 530/380; 514/1; 514/2; 514/8; 514/12; 424/94.1; 424/94.3; 424/94.64; 436/64; 436/86

(58) Field of Classification Search .............. 514/1, 514/2, 8, 12; 530/350, 380; 424/94, 64, 424/94.1, 94.3; 436/64, 86
See application file for complete search history.

(56) References Cited

U.S. PATENT DOCUMENTS 5,837,682 A * 11/1998 Folkman et al. ............. 514/12

2003/0012792 A1 * 1/2003 Holaday et al. ......... 424/185.1

FOREIGN PATENT DOCUMENTS

| DE | 4423574 A1 | 1/1996 |
|---|---|---|
| EP | 0299706 A2 | 1/1989 |
| EP | 0370711 A1 | 5/1990 |
| WO | 96/35774 A2 | 11/1996 |
| WO | 98/54217 A1 | 12/1998 |
| WO | 99/00420 A1 | 1/1999 |

OTHER PUBLICATIONS

Amino acid database, Accession No. P00747, Jul. 21, 1986.*

Sim, B. Kim Lee et al. A recombinant human angiostatin protein inhibits experimental primary and metastatic cancer. Cancer research 57:1329-1334, Apr. 1, 1997.*

Sequence alignment between Applicants' SEQ ID No.: 2 and U.S. 20030012792 A1, sequence No. 61, 2003.*

Cao et al. Kringle structures and antiangiogenesis. Curr. Med. Chem.-Anti-Cancer Agents 2: 667-681, Aug. 2002.*

Cao, Y. et al., Kringle Domains of Human Angiostatin, *The Journal of Biological Chemistry*, vol./Iss: 271 (46), pp. 29461-29467, Nov. 15, 1996.

* cited by examiner

*Primary Examiner*—Alana M. Harris
(74) *Attorney, Agent, or Firm*—Kilpatrick Stockton LLP

(57) ABSTRACT

Disclosed are deglycosylated fragments of a kringle 1-3 region of plasminogen, nucleotides encoding deglycosylated kringle 1-3 region proteins and antibodies specific for deglycosylated kringle 1-3 region proteins. The compositions of the present invention have increased antiangiogenic activity as compared to previously isolated kringle 1-3 region proteins. Also included in the present invention are methods of treating angiogenesis-associated diseases and conditions such as cancer using the compositions described herein.

20 Claims, 4 Drawing Sheets

SEQ ID NO:2
VYLSECKTGNGKNYRGTMSKTKNGITCQKWSSTSPHRP
RFSPATHPSEGLEENYCRNPDNDPQGPWCYTTDPEKRYD
YCDILECEEECMHCSGENYDGKISKTMSGLECQAWDSQ
SPHAHGYIPSKFPNKNLKKNYCRNPDRELRPWCFTTDPN
KRWELCDIPRCTTPPPSSGPTYQCLKGTGENYRGNVAVT
VSGHTCQHWSAQTPHTHERTPENFPCKNLDENYCRNPD
GKRAPWCHTTNSQVRWEYCKIPSCDSSPV

SEQ ID NO:1
GTGTATCTCTCAGAGTGCAAGACTGGGAATGGAAAGA
ATTACAGAGGGACGATGTCCAAAACAAAAAATGGCAT
CACCTGTCAAAAATGGAGTTCCACTTCTCCCCACAGA
CCTAGATTCTCACCTGCTACACACCCCTCAGAGGGACT
GGAGGAGAACTACTGCAGGAATCCAGACAACGATCC
GCAGGGGCCCTGGTGCTATACTACTGATCCAGAAAAG
AGATATGACTACTGCGACATTCTTGAGTGTGAAGAGG
AATGTATGCATTGCAGTGGAGAAAACTATGACGGCAA
AATTTCCAAGACCATGTCTGGACTGGAATGCCAGGCC
TGGGACTCTCAGAGCCCACACGCTCATGGATACATTC
CTTCCAAATTTCCAAACAAGAACCTGAAGAAGAATTA
CTGTCGTAACCCCGATAGGGAGCTGCGGCCTTGGTGT
TTCACCACCGACCCCAACAAGCGCTGGGAACTTTGTG
ACATCCCCCGCTGCACAACACCTCCACCATCTTCTGGT
CCCACCTACCAGTGTCTGAAGGGAACAGGTGAAAACT
ATCGCGGGAATGTGGCTGTTACCGTGTCCGGGCACAC
CTGTCAGCACTGGAGTGCACAGACCCCTCACACACAT
GAAAGGACACCAGAAAACTTCCCCTGCAAAAATTTGG
ATGAAAACTACTGCCGCAATCCTGACGGAAAAAGGGC
CCCATGGTGCCATACAACCAACAGCCAAGTGCGGTGG
GAGTACTGTAAGATACCGTCCTGTGACTCCTCCCAGT
A

Figure 1

DEGLYCOSYLATED KRINGLE 1-3 REGION FRAGMENTS OF PLASMINOGEN AND METHODS OF USE

CROSS REFERENCE TO RELATED APPLICATIONS

This application claims priority to U.S. Provisional Patent Application Ser. No. 60/119,562, filed Feb. 10, 1999 and U.S. Provisional Patent Application Ser. No. 60/128,062, filed Apr. 7, 1999.

This invention was made with government support under Grant No.(s) CA 45548 by the NIH. The government may have certain rights in the invention.

FIELD OF THE INVENTION

The present invention relates to compositions and methods for the modulation of angiogenesis. More particularly, the present invention relates to deglycosylated kringle 1-3 region proteins that are useful for the treatment of angiogenesis-associated diseases such as cancer.

BACKGROUND OF THE INVENTION

As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. However, angiogenesis also occurs under abnormal or undesired conditions such as during tumor development, growth and metastasis. This type of angiogenesis may also be referred to as uncontrolled angiogenesis.

Both controlled and uncontrolled angiogenesis are thought to proceed in a similar manner. Endothelial cells and pericytes surrounded by a basement membrane form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, tumor metastasis and abnormal growth by endothelial cells. The diverse pathological disease states in which unregulated angiogenesis is present have been grouped together as angiogenic dependent or angiogenic associated diseases. The hypothesis that tumor growth is angiogenesis-dependent was first proposed in 1971 by M. Judah Folkman. (Folkman J., "Tumor angiogenesis: Therapeutic implications" *N. Engl. Jour. Med* 285: 1182–1186 (1971)). In its simplest terms the hypothesis states: "Once tumor 'take' has occurred, every increase in tumor cell population must be preceded by an increase in new capillaries converging on the tumor." Tumor 'take' is currently understood to indicate a pre-vascular phase of tumor growth in which a population of tumor cells occupying a few cubic millimeters volume and not exceeding a few million cells, can survive on existing host microvessels. Expansion of tumor volume beyond this phase requires the induction of new capillary blood vessels.

Several molecules have been discovered that inhibit angiogenesis, inhibit tumor growth, cause regression of primary tumors, and/or inhibit metastasis of primary tumors. These molecules are called antiangiogenic agents. One of these antiangiogenic agents has been termed angiostatin, which is a fragment of a plasminogen protein. Angiostatin was first described in U.S. Pat. No. 5,639,725.

Plasminogen protein comprises five kringle region domains and a serine protease domain located at the carboxy-terminal region. The DNA sequence of human plasminogen has been published. (Browne, M. J., et al., "Expression of recombinant human plasminogen and aglycoplasminogen in HeLa cells" *Fibrinolysis* 5(4):257–260 (1991)). Each kringle region of the plasminogen molecule contains approximately 80 amino acids and contains 3 disulfide bonds. (Robbins, K. C., "The plasminogen-plasmin enzyme system" *Hemostasis and Thrombosis*) Basic Principles and Practice, 2nd Edition, ed. by Colman, R. W. et al. J. B. Lippincott Company, pp. 340–357, 1987). The approximate amino acid spans of each kringle domain of human plasminogen are as follows: kringle 1 typically encompasses Cys84–Cys162, kringle 2 typically encompasses Cys166–Cys243, kringle 3 typically encompasses Cys256–Cys333, kringle 4 typically encompasses Cys358–Cys435, and kringle 5 typically encompasses Cys462–Cys541. (Castellino, F. J. and McCance, S. G., "The kringle domains of human plasminogen" *Ciba Found. Symp.*, 212:46–65 (1997)). Because each kringle domain is separated by an approximately 20 amino acid inter-kringle domain, a kringle region as herein defined can include any portion of these adjacent inter-kringle domains.

Angiostatin protein comprises one or more of these five kringle regions of plasminogen. Among the proteases suggested to be responsible for angiostatin generation are macrophage metalloelastase, metalloproteinases (mmp's) –3, –7, and –9 and plasmin itself in the presence of a free sulphydryl donor such as cysteine. (Dong, Z. et al. "Macrophage-derived metalloelastase is responsible for the generation of angiostatin in Lewis lung carcinoma" *Cell*, 88:801–810 (1997); Lijnen, H. R. et al., "Generation of an angiostatin-like fragment from plasminogen by stromelysin-1 (MMP-3)" *Biochemistry*, 37:4699–4702 (1998); Patterson, B. C. and Sang Q. A., "Angiostatin-converting enzyme activities of human matrilysis (MMP-7) and gelatinase B/type IV collagenase (MMP-9)" *J. Biol. Chem.* 272: 28823–28825 (1997)) (Stathakis, P. et al., "Generation of angiostatin by reduction and proteolysis of plasmin" *J. Biol. Chem.* 272:20641–20645 (1997); Gately, S. et al., "The mechanism of cancer-mediated conversion of plasminogen to that angiogenesis inhibitor angiostatin" *Proc. Natl. Acad. Sci. USA* 94:10868–10872 (1997)).

In its glycosylated state, human plasminogen protein contains an N-linked carbohydrate chain at amino acid position Asn-289 and two O-linked mucin type carbohydrate chains at amino acid positions Ser-249 and Thr-346. Since angiostatin protein is a fragment of a plasminogen protein, angiostatin protein also contains the above-described carbohydrate chains. The proteolytic digestion of plasminogen, by tPA and uPA to produce plasmin for example, is known to be modulated by the carbohydrate content of plasminogen. Further the carbohydrate chains are known to modulate binding of plasminogen to cell surface receptors. Carbohydrate is also known to play a general role in systemic half life of circulating proteins. (Mori, K. et al., "The activation of type 1 and type 2 plasminogen by type I and type II tissue plasminogen activator" *J. Biol. Chem.* 270:3261–3267 (1995); Davidson, D. J. and Castellino, F. J., "The influence of the nature of the asparagine 289-linked oligosaccharide on the activation by urokinase and lysine binding properties of natural and recombinant human plasminogens" *J. Clin. Invest.* 92:249–254 (1993); Edelberg, J. et al. "Neonatal plasminogen displays altered cell surface binding and activation kinetics" *J. Clin. Invest.* 86:107–112 (1990); Gonzales-Gronow, M. et al. "Further characterization of the cellular plasminogen binding site: evidence that plasminogen 2 and lipoprotein a compete for the same site" *Biochemistry,* 28:2374–2377 (1989); Jenkins, N. et al. "Getting the glycosylation right: implications for the biotechnology industry" *Nat. Biotechnol.* 14:975–981 (1996)).

The mechanism underlying how angiostatin and its related kringle fragments specifically inhibit endothelial cell growth remains uncharacterized. It is not yet clear whether the inhibition is mediated by a receptor that is specifically expressed in proliferating endothelial cells, or if angiostatin is internalized by endothelial cells and subsequently inhibits cell proliferation. Alternatively, angiostatin may interact with an endothelial cell adhesion receptor such as integrin $a_v b_3$, blocking integrin-mediated angiogenesis (Brooks, P. C., et al. "Integrin alpha v beta 3 antagonists promote tumor regression by inducing apoptosis of angiogenic blood vessels" *Cell* 79:1157–1164 (1994)).

Although angiostatin has been identified as an angiogenesis inhibitor, what is needed in the art are kringle region fragments of plasminogen that have increased antiangiogenic activity. These improved kringle region proteins should be useful for the treatment of angiogenesis-mediated diseases, such as cancer, and for the modulation of other angiogenic processes, such as wound healing and reproduction. Due to the improved nature of the antiangiogenic kringle region proteins, these proteins should be able to be administered in smaller doses, thus lowering the cost of cancer treatment. What is also needed in the art are compositions and methods for the detection, measurement and localization of improved antiangiogenic kringle region proteins.

SUMMARY OF THE INVENTION

Compositions and methods are provided herein that are effective for modulating angiogenesis, and inhibiting unwanted angiogenesis, especially angiogenesis related to tumor growth. In particular, the present invention provides deglycosylated kringle 1-3 region proteins that are fragments of plasminogen. It is a surprising discovery of the present invention that deglycosylation of kringle 1-3 region proteins dramatically increases the antiangiogenic activity of these proteins. It is to be understood that the deglycosylated kringle 1-3 region proteins described herein include fusion proteins wherein a deglycosylated kringle 1-3 region protein is contiguous with one or more other proteins. In a preferred embodiment, the fusion protein comprises a deglycosylated kringle 1-3 region protein and another antiangiogenic protein.

Also included in the present invention are nucleotides encoding the deglycosylated kringle 1-3 region proteins, expression vectors containing DNA sequences encoding deglycosylated kringle 1-3 region proteins, and cells containing one or more expression vectors containing DNA sequences encoding deglycosylated kringle 1-3 region proteins.

The present invention also includes antibodies specific for the deglycosylated kringle 1-3 region proteins, antibodies that inhibit the binding of antibodies specific for deglycosylated kringle 1-3 region proteins, and antibodies specific for a deglycosylated kringle 1-3 region protein receptor. These antibodies can be polyclonal antibodies or monoclonal antibodies. The antibodies specific for the deglycosylated kringle 1-3 region proteins can be used in diagnostic kits to detect the presence and quantity of deglycosylated kringle 1-3 region proteins which is diagnostic or prognostic for the occurrence or recurrence of cancer or other diseases mediated by angiogenesis. Antibodies specific for deglycosylated kringle 1-3 region proteins may also be administered to a human or animal to passively immunize the human or animal against deglycosylated kringle 1-3 region proteins, thereby reducing angiogenic inhibition.

The present invention provides methods and compositions for treating diseases and processes mediated by undesired and uncontrolled angiogenesis by increasing an in vivo concentration of deglycosylated kringle 1-3 region protein in a human or animal. In vivo concentrations of deglycosylated kringle 1-3 region proteins may be increased by administering to a human or animal a composition comprising a substantially purified deglycosylated kringle 1-3 region protein in a dosage sufficient to inhibit angiogenesis. Additionally, in vivo concentrations of deglycosylated kringle 1-3 region proteins may be increased in a human or animal by the administration of nucleotides encoding deglycosylated kringle 1-3 region proteins or enzymes that release deglycosylated kringle 1-3 region proteins from plasminogen or plasmin. The present invention is particularly useful for treating or repressing the growth of tumors.

Accordingly, it is an object of the present invention to provide a composition comprising a deglycosylated kringle 1-3 region protein.

It is another object of the present invention to provide a nucleotide composition encoding a deglycosylated kringle 1-3 region protein.

It is another object of the present invention to provide compositions and methods for increasing an in vivo concentration of deglycosylated kringle 1-3 region proteins.

It is another object of the present invention to provide a composition comprising an antibody to a deglycosylated kringle 1-3 region protein that is specific for the deglycosylated kringle 1-3 region protein and does not recognize plasminogen.

It is an object of present invention to provide a method for detecting and quantifying the presence of an antibody specific for a deglycosylated kringle 1-3 region protein in a body fluid.

It is another object of the present invention to provide a method for the detection or prognosis of cancer.

It is another object of the present invention to provide a method of treating diseases and processes that are mediated by angiogenesis.

It is another object of the present invention to provide a composition for treating or repressing the growth of a cancer.

Yet another object of the invention is to provide compositions and methods useful for gene therapy for the modulation of angiogenic processes.

These and other objects, features and advantages of the present invention will become apparent after a review of the following detailed description of the disclosed embodiments and the appended claims.

BRIEF DESCRIPTION OF THE FIGURES

FIG. 1 shows the amino acid sequence (SEQ ID NO:2) and nucleotide sequence (SEQ ID NO: 1) encoding a preferred deglycosylated kringle 1-3 region protein.

DETAILED DESCRIPTION

Figure 2:
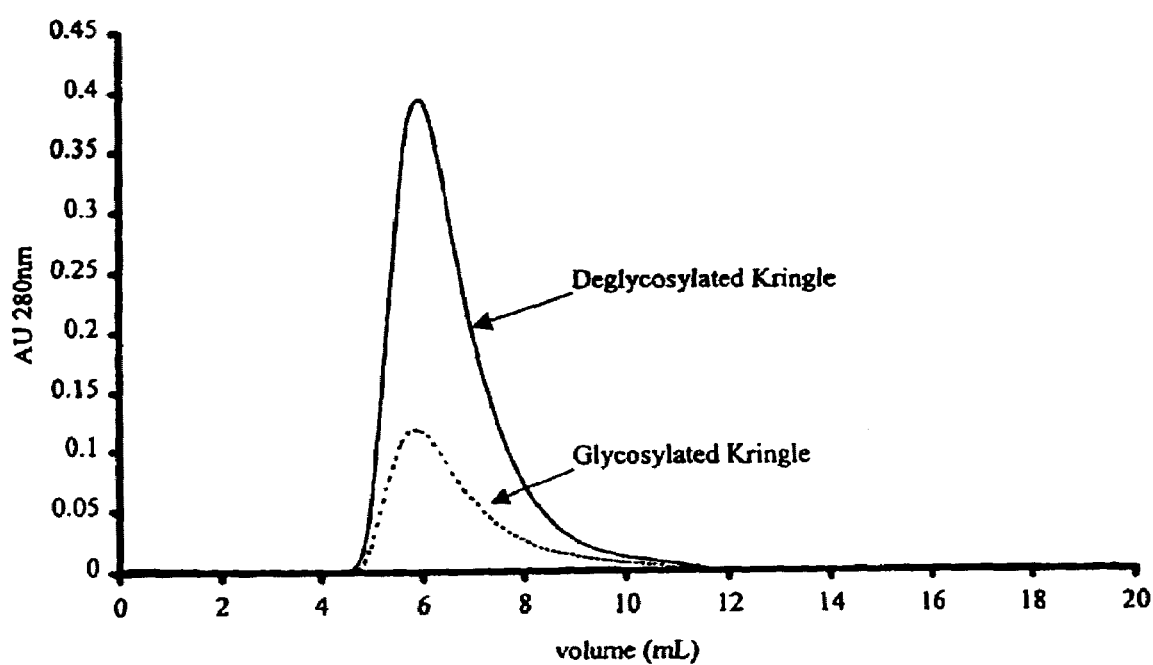
FIG. 2 shows the purification of glycosylated and deglycosylated kringle 1-3 region proteins using lys-Sepharose.

The present invention includes deglycosylated fragments of a kringle 1-3 region of a plasminogen protein. Also included in the present invention are methods of using the deglycosylated kringle 1-3 region proteins and methods and compositions for detecting the deglycosylated kringle 1-3 region proteins.

A surprising discovery of the present invention is that deglycosylated fragments of the kringle 1-3 region of plasminogen are dramatically more antiangiogenic than glycosylated fragments of the kringle 1-3 region of plasminogen. Accordingly, the present invention includes deglycosylated fragments of kringle 1-3 region proteins and compositions comprising deglycosylated fragments of kringle 1-3 region proteins. In one embodiment, a composition comprises a pharmaceutically acceptable carrier and a deglycosylated fragment of a kringle 1-3 region of a plasminogen protein in a greater concentration than a naturally glycosylated form of the deglycosylated fragment, wherein the deglycosylated fragment lacks one or more carbohydrate moieties linked to the naturally glycosylated form and wherein the deglycosylated fragment has antiangiogenic activity. In a further embodiment, the ratio of the amount of the deglycosylated fragment to the amount of the naturally glycosylated form is at least 60:40, more preferably at least 80:20, and most preferably 100:0. The ratio of the deglycosylated fragment to the naturally glycosylated form may also be at least 95:5, 96:4, 97:3, 98:2 and 99:1.

As used herein, the term "deglycosylated" refers to a protein or peptide lacking one or more carbohydrate moieties that are linked to a naturally glycosylated form of a kringle 1-3 region proteins. A "naturally glycosylated form" refers to a fragment of a kringle 1-3 region protein, or a larger protein from which the kringle 1-3 region fragment is derived, that is glycosylated at amino acid positions as found in nature. For example, one naturally glycosylated form of human plasminogen is glycosylated at Ser-249, Asn-289, and Thr-346, and therefore, the naturally glycosylated form of fragments of a kringle 1-3 region of human plasminogen are glycosylated at Ser-249, Asn-289, and/or Thr-346. It is to be understood that the naturally glycosylated forms of the kringle 1-3 region fragments described herein are not required to exist as a fragment in nature and can exist in nature as part of a larger protein.

Therefore, "deglycosylated plasminogen" refers to a plasminogen protein of any species that lacks carbohydrate at a position that may be otherwise glycosylated in nature (i.e., that is glycosylated in a naturally glycosylated form of the plasminogen protein). For example, included in the present invention is a plasminogen protein lacking a bisialylated-biantennary glycan at an amino acid position corresponding to amino acid position 289 of human plasminogen (Asn-289), an O-linked mucin type carbohydrate chain at an amino acid position corresponding to amino acid position 249 of human plasminogen (Ser-249), and/or an O-linked mucin type carbohydrate chain at an amino acid position corresponding to amino acid position 346 of human plasminogen (Thr-346). Additionally, the term "deglycosylated plasminogen" encompasses a plasminogen protein having zero, one or two carbohydrate chains. In one embodiment of the present invention, a deglycosylated plasminogen lacks any N-linked carbohydrate chain at amino acid corresponding to amino acid position 289 of human plasminogen. In a further embodiment, a deglycosylated plasminogen lacks any carbohydrate moiety at an amino acid position corresponding to amino acid position 289 of human plasminogen.

As also used herein, the terms "deglycosylated kringle 1-3 region protein" and "deglycosylated fragment" refer to a fragment of a kringle 1-3 region of a plasminogen protein of any species that lacks carbohydrate at a position that may be otherwise glycosylated in nature (i.e., that is glycosylated in a naturally glycosylated form of the deglycosylated kringle 1-3 region protein). For example, included herein are deglycosylated kringle 1-3 region proteins that lack a bisialylated-biantennary glycan at an amino acid position corresponding to amino acid position 289 of human plasminogen, an O-linked mucin type carbohydrate chain at amino acid position corresponding to amino acid position 249 of human plasminogen, and/or an O-linked mucin type carbohydrate chain at amino acid position corresponding to amino acid position 346 of human plasminogen. Therefore, the term "deglycosylated kringle 1-3 region protein" encompasses a kringle 1-3 protein having zero, one or two carbohydrate chains. In one embodiment of the present invention, the deglycosylated kringle 1-3 region protein lacks a bisialylated-biantennary glycan at amino acid position 289. In another embodiment, the carbohydrate chain at amino acid position 289 is smaller than a bisialylated-biantennary glycan. In another embodiment, the deglycosylated kringle 1-3 region protein lacks a carbohydrate moiety at an amino acid position corresponding to amino acid position 289 of human plasminogen.

"Corresponding to", when referring to amino acids, indicates the comparison of two amino acids in the same region of different proteins, or fragments thereof, wherein the proteins are homologs, orthologs or paralogs. Homologs are defined as proteins with substantial homology, wherein "substantial homology" is defined below. Orthologs are defined as proteins having non-identical amino acid sequences and similar functional characteristics, wherein the proteins are from different species, but wherein the species have a common ancestral origin. Paralogs are defined as proteins having non-identical amino acid sequences and similar functional characteristics, wherein the proteins are from the same species. In the present invention, an example of an amino acid corresponding to Asn-289 located in kringle 3 of human plasminogen is an amino acid located in kringle 3 of murine plasminogen that can have an N-linked carbohydrate moiety attached thereto, and preferably a bisialylated-biantennary glycan attached thereto, as found in nature. It is to be understood that the present invention includes fragments of kringle 1-3 regions of a plasminogen from a species other than a human.

In another embodiment of the present invention, the kringle 1-3 region protein has a modified amino acid at a position corresponding to position 289 of human plasminogen such that a carbohydrate moiety is not added to that position during post-translational modification of the protein. In a preferred embodiment, the amino acid substitution is a conservative substitution. In a further preferred embodiment, the amino acid substitution is from asparagine to glutamic acid. In yet a further preferred embodiment, the kringle 1-3 region protein has the amino acid sequence as shown in SEQ ID NO:2 that corresponds to an approximately kringle 1-3 region.

The deglycosylated kringle 1-3 region proteins of the present invention can be made in vivo or in vitro. For example, the deglycosylated kringle 1-3 region proteins can be isolated from body fluids including, but not limited to, serum, urine and ascites, or synthesized by chemical or biological methods (e.g. recombinant gene expression, chemical synthesis of oligonucleotides, and in vitro enzymatic catalysis of larger proteins such as plasminogen or plasmin). Recombinant techniques include gene amplification from DNA sources using the polymerase chain reaction (PCR), and gene amplification from RNA sources using reverse transcriptase/PCR. For example, a deglycosylated kringle 1-3 region protein can be recombinantly produced by expressing a gene encoding the protein, wherein an amino acid position that can be glycosylated in nature is substituted for an amino acid that is not glycosylated. This gene may be administered to an individual using the gene therapy methods described in more detail below. The kringle 1-3 region proteins can also be made in vivo by the administration of deglycosylated plasminogen and an enzyme that cleaves deglycosylated plasminogen to an individual. In a preferred embodiment, the enzyme is an elastase enzyme such as macrophage metalloelastase. Deglycosylated kringle 1-3 proteins can also be made in vivo by the administration of an enzyme that specifically cleaves deglycosylated plasminogen.

When isolating deglycosylated kringle 1-3 region proteins from larger proteins such as plasminogen or plasmin, either the plasminogen or plasmin may be deglycosylated prior to enzymatic catalysis or the resulting kringle 1-3 region protein itself may be deglycosylated. Methods for deglycosylation of proteins are well known to those skilled in the art. However, it is a surprising discovery of the present invention that there is an increased yield of kringle 1-3 region proteins following enzymatic catalysis of deglycosylated plasminogen by elastase as compared to enzymatic catalysis of glycosylated plasminogen by elastase. Therefore, in a preferred embodiment of the present invention, kringle 1-3 region proteins are isolated by elastase digestion of deglycosylated plasminogen.

It is to be understood that "kringle 1-3 region" is defined herein as a region that corresponds to approximately amino acid position 1 through approximately amino acid position 333 of human plasminogen. Thus, the deglycosylated fragments of the kringle 1-3 region of the present invention may contain the N-terminal sequence proceeding the kringle 1 region, kringle regions 1, 2, and 3, inter-kringle regions, and antiangiogenic fragments thereof, wherein the aforementioned regions are found in nature as contiguous sequences or not. Antiangiogenic fragments of the kringle 1-3 region that can be deglycosylated are further disclosed in U.S. Pat. Nos. 5,639,725 and 5,837,682.

It is also to be understood that the present invention is contemplated to include any deglycosylated kringle 1-3 region protein derivatives. A kringle 1-3 region protein derivative includes a protein having the amino acid sequence of a kringle 1-3 region of a plasminogen protein. A kringle 1-3 region protein derivative also includes a peptide having a sequence corresponding to an antiangiogenic fragment a kringle 1-3 region. An "antiangiogenic fragment" is defined to be a peptide whose amino acid sequence corresponds to a subsequence of a kringle 1-3 region, referred to as an "antiangiogenic subsequence". A "subsequence" is a sequence of contiguous amino acids found within a larger sequence. A subsequence is generally composed of approximately at least 70%, more preferably 80%, and most preferably 90% of the larger sequence.

A kringle 1-3 region protein derivative also includes a protein or peptide having a modified sequence in which one or more amino acids in the original sequence or subsequence have been substituted with a naturally occurring amino acid residue or amino acid residue analog (also referred to as modified amino acid). Suitable kringle 1-3 region protein derivatives have modified sequences which are substantially homologous to the amino acid sequence of a kringle 1-3 region protein or to an antiangiogenic subsequence of a kringle 1-3 region protein.

An "amino acid residue" is a moiety found within a protein or peptide and is represented by —NH—CHR—CO—, wherein R is the side chain of a naturally occurring amino acid. When referring to a moiety found within a peptide, the terms "amino acid residue" and "amino acid" are used interchangeably. An "amino acid residue analog" includes D or L configurations having the following formula: —NH—CHR—CO—, wherein R is an aliphatic group, a substituted aliphatic aromatic group, a benzyl group, a substituted benzyl group, an aromatic group or a substituted aromatic group and wherein R does not correspond to the side chain of a naturally occurring amino acid.

Suitable substitutions for amino acid residues in the sequence of the deglycosylated kringle 1-3 region proteins described herein include conservative substitutions that result in angiogenic deglycosylated kringle 1-3 region protein derivatives. A conservative substitution is a substitution in which the substituting amino acid (naturally occurring or modified) is structurally related to the amino acid being substituted. "Structurally related" amino acids are approximately the same size and have the same or similar functional groups in the side chains.

Provided below are groups of naturally occurring and modified amino acids in which each amino acid in a group has similar electronic and steric properties. Thus, a conservative substitution can be made by substituting an amino acid with another amino acid from the same group. It is to be understood that these groups are non-limiting and that additional modified amino acids could be included in each group.

Group I includes leucine, isoleucine, valine, methionine and modified amino acids having the following side chains: ethyl, n-propyl n-butyl. Preferably, Group I includes leucine, isoleucine, valine and methionine.

Group II includes glycine, alanine, valine and a modified amino acid having an ethyl side chain. Preferably, Group II includes glycine and alanine.

Group III includes phenylalanine, phenylglycine, tyrosine, tryptophan, cyclohexylmethyl, and modified amino residues having substituted benzyl or phenyl side chains. Preferred substituents include one or more of the following: halogen, methyl, ethyl, nitro, —NH$_2$, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester of glutamic or aspartic acid (e.g., methyl, ethyl, n-propyl iso-propyl, cyclohexyl, benzyl or substituted benzyl), glutamine, asparagine, —CO—NH-alkylated glutamine or asparagine (e.g., methyl, ethyl, n-propyl and iso-propyl) and modified amino acids having the side chain —(CH$_2$)$_3$—

COOH, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, methyl aspartate, ethyl aspartate, benzyl aspartate and methyl glutamate, ethyl glutamate and benzyl glutamate, glutamine and asparagine.

Group V includes histidine, lysine, ornithine, arginine, N-nitroarginine, β-cycloarginine, γ-hydroxyarginine, N-amidinocitruline and 2-amino-4-guanidinobutanoic acid, homologs of lysine, homologs of arginine and homologs of ornithine. Preferably, Group V includes histidine, lysine, arginine and ornithine. A homolog of an amino acid includes from 1 to about 3 additional or subtracted methylene units in the side chain.

Group VI includes serine, threonine, cysteine and modified amino acids having C1–C5 straight or branched alkyl side chains substituted with —OH or —SH, for example, —CH$_2$CH$_2$OH, —CH$_2$CH$_2$CH$_2$OH or —CH$_2$CH$_2$OHCH$_3$. Preferably, Group VI includes serine, cysteine or threonine.

In another aspect of the present invention, suitable substitutions for amino acid residues in the amino acid sequences described herein include "severe substitutions" that result in kringle 1-3 region protein derivatives that are antiangiogenic. Severe substitutions that result in antiangiogenic kringle 1-3 region protein derivatives are much more likely to be possible in positions that are not highly conserved than at positions that are highly conserved. In the present invention, severe substitutions are much more likely to be possible in the inter-kringle regions and the N-terminal sequence proceeding kringle 1. A "severe substitution" is a substitution in which the substituting amino acid (naturally occurring or modified) has significantly different size and/or electronic properties compared with the amino acid being substituted. For example, the side chain of the substituting amino acid can be significantly larger (or smaller) than the side chain of the amino acid being substituted and/or can have functional groups with significantly different electronic properties than the amino acid being substituted.

Examples of severe substitutions of this type include the substitution of phenylalanine or cyclohexylmethyl glycine for alanine, isoleucine for glycine, a D amino acid for the corresponding L amino acid or —NH—CH[(—CH$_2$)$_5$—COOH]—CO— for aspartic acid. Alternatively, a functional group may be added to the side chain, deleted from the side chain or exchanged with another functional group. Examples of severe substitutions of this type include adding an amine or hydroxyl, carboxylic acid to the aliphatic side chain of valine, leucine or isoleucine, exchanging the carboxylic acid in the side chain of aspartic acid or glutamic acid with an amine or deleting the amine group in the side chain of lysine or ornithine. In yet another alternative, the side chain of the substituting amino acid can have significantly different steric and electronic properties that the functional group of the amino acid being substituted. Examples of such modifications include tryptophan for glycine, lysine for aspartic acid and —(CH$_2$)$_4$COOH for the side chain of serine. These examples are not meant to be limiting.

"Substantial homology" exists between two amino acid sequences when a sufficient number of amino acid residues at corresponding positions of each amino acid sequence are either identical or structurally related such that a protein or peptide having the first amino acid sequence and a protein or peptide having the second amino acid sequence exhibit similar biological activities. Generally, there is substantial sequence homology among the amino acid sequences when at least 30%, more preferably at least 40%, and most preferably at least 50%, of the amino acids in the first amino acid sequence are identical to or structurally related to the second amino acid sequence. Homology is often measured using sequence analysis software, e.g., BLASTIN or BLASTP (available at the National Instititutes of Health (NIH) World Wide Web Server. The default parameters for comparing the two sequences (e.g., "Blast"-ing two sequences against each other) by BLASTIN (for nucleotide sequences) are reward for match=1, penalty for mismatch =–2, open gap=5, and extension gap ~2. When using BLASTP for protein sequences, the default parameters are reward for match=0, penalty for mismatch=0, open gap=11, and extension gap=1.

With regard to the present invention, the kringle region motif of kringles 1-3 of a plasminogen protein is also known to exist in other biologically active proteins. These proteins include, but are not limited to, prothrombin, hepatocyte growth factor, scatter factor and macrophage stimulating protein. (Yoshimura, T, et al., "Cloning, sequencing, and expression of human macrophage stimulating protein (MSP, MST1) confirms MSP as a member of the family of kringle proteins and locates the MSP gene on Chromosome 3" *J. Biol. Chem.*, 268:15461–15468, (1993)). It is contemplated that any kringle 1-3 region protein or peptide having a three-dimensional kringle-like conformation or cysteine motif that has antiangiogenic activity in vivo, is part of the present invention.

It is to be understood that as used herein, the term "isolated" refers to a composition which is substantially or essentially free from at least some of the components that normally accompany it in its native state. Thus, the deglycosylated kringle 1-3 region proteins of this invention do not contain some of the materials normally associated with their in situ environment. Typically, the isolated, deglycosylated kringle region 1-3 proteins of the invention are at least about 80% pure, usually at least about 90% pure, and preferably at least about 95% pure as measured by band intensity on a silver stained gel. It is to be understood that the term "isolated" does not exclude fusion proteins comprising the deglycosylated kringle 1-3 region proteins from the present invention. The present invention contemplates fusion proteins, or chimeric proteins, comprising the kringle 1-3 region proteins described herein and other proteins. In a preferred embodiment the fusion proteins comprise deglycosylated kringle 1-3 region proteins and other antiangiogenic proteins such as endostatin proteins, wherein the endostatin proteins are defined as antiangiogenic fragments of the C-terminal non-collagenous region of a collagen protein.

The deglycosylated kringle 1-3 region proteins described herein are useful for treating diseases or processes that are mediated by, or involve, angiogenesis. In particular, the deglycosylated kringle 1-3 region proteins are useful for the treatment of angiogenesis-mediated cancers. The deglycosylated kringle 1-3 region proteins are also useful for the generation of antibodies specific for the deglycosylated kringle 1-3 region proteins, and for the identification and isolation of receptors for and chemical mimetics of deglycosylated kringle 1-3 region proteins.

In addition to deglycosylated kringle 1-3 region proteins, the present invention encompasses compositions comprising nucleotide sequences encoding the kringle 1-3 region proteins described herein. In one embodiment of the present invention, the nucleotide sequence encodes a kringle 1-3 region protein containing a modified amino acid at a position corresponding to amino acid 289 of human plasminogen. In a preferred embodiment, the nucleotide sequence is as shown in SEQ ID NO: 1. The present invention also includes a vector containing a DNA sequence encoding a kringle 1-3 region protein, wherein the vector is capable of expressing kringle 1-3 region proteins when present in a cell. The cell may contain one vector or multiple vectors. The nucleotide sequences described herein are useful for recombinantly producing the deglycosylated kringle 1-3 region proteins of the present invention and for treatment of angiogenesis associated diseases and conditions via gene therapy.

Still further, the deglycosylated kringle 1-3 region proteins can be used to generate antibodies to the deglycosylated kringle 1-3 region proteins and their receptors. In particular, an antibody can be generated that specifically binds to a deglycosylated kringle 1-3 region but does not bind to glycosylated plasminogen or a glycosylated kringle 1-3 region protein. The terms "antibody" and "antibodies" as used herein include monoclonal, polyclonal, chimeric, single chain, bispecific, simianized, and humanized antibodies as well as Fab fragments, including the products of an Fab immunoglobulin expression library.

To enhance the potential for high specificity in the development of antisera (or agonists and antagonists) to deglycosylated kringle 1-3 region proteins, protein sequences can be compared to known sequences using protein sequence databases such as GenBank, Brookhaven Protein, SWISS-PROT, and PIR to determine potential sequence homologies. This information facilitates elimination of sequences that exhibit a high degree of sequence homology to other molecules. These antibodies that specifically bind to the deglycosylated kringle 1-3 region proteins or their receptors, can be used in diagnostic methods and kits that are well known to those of ordinary skill in the art to detect or quantify the deglycosylated kringle 1-3 region proteins or their receptors in a body fluid or tissue. Results from these tests can be used to diagnose or predict the occurrence or recurrence of a cancer or other angiogenic-mediated disease.

The phrases "specifically binds to" or "specific for" when referring to an antibody refers to a binding reaction which is determinative of the presence of the peptide in the presence of a heterogeneous population of proteins and other biologics. Thus, under designated immunoassay conditions, the specified antibodies bind preferentially to a particular peptide and do not bind in a significant amount to other proteins present in the sample. Specific binding to a peptide under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See, Harlow and Lane (1988) *Antibodies, A Laboratory Manual*, Cold Spring Harbor Publications, New York, for a description of immunoassay formats and conditions that can be used to determine specific immunoreactivity.

When labeled with a detectable biomolecule or chemical, the deglycosylated kringle 1-3 region proteins, nucleic acids and antibodies described above are useful for purposes such as in vivo and in vitro diagnostics and laboratory research using the methods and assays described below. Various types of labels and methods of conjugating the labels to the polypeptides and antibodies are well known to those skilled in the art. Examples of labels include, but are not limited to, radiolabels, bioluminescent labels, fluorogens and chromogens. Still further, the present invention encompasses deglycosylated kringle 1-3 region proteins, deglycosylated kringle 1-3 region protein antisera, deglycosylated kringle 1-3 region protein receptor agonists or deglycosylated kringle 1-3 region protein receptor antagonists that are combined with pharmaceutically acceptable excipients, and optionally sustained-release compounds or compositions, such as biodegradable polymers, to form therapeutic compositions for use in the methods of treatment described below.

The methods of the present invention include methods of making, detecting and measuring the deglycosylated kringle 1-3 region proteins of the present invention as well as methods of treating angiogenesis associated conditions and diseases using the deglycosylated kringle 1-3 region proteins of the present invention. Deglycosylated kringle 1-3 region proteins can be produced synthetically by chemical reaction or by recombinant techniques in conjunction with expression systems. These deglycosylated kringle 1-3 region proteins can be animal or human in origin. In one embodiment, the deglycosylated kringle 1-3 region protein is produced recombinantly and has the amino acid sequence of SEQ ID NO: 1.

Deglycosylated kringle 1-3 region proteins may also be produced in vitro or in vivo by enzymatically cleaving plasminogen or plasmin to generate proteins having antiangiogenic activity or by using compounds that mimic the action of endogenous enzymes that cleave deglycosylated plasminogen into deglycosylated kringle 1-3 region proteins. Deglycosylated kringle 1-3 region protein production may also be modulated by compounds that affect the activity of plasminogen cleaving enzymes. In particular, it is a surprising discovery of the present invention that glycosylation of plasminogen reduces the yield of kringle 1-3 region proteins upon cleavage of plasminogen with elastase. Therefore, in one embodiment of the present invention, the method of making deglycosylated kringle 1-3 region proteins comprises cleaving deglycosylated plasminogen with elastase. Given the role of elastase reported here in the generation of kringle 1-3 region proteins, it is likely that the N-linked carbohydrate on kringle 3 will also modulate the reaction mechanism of other proteinases potentially responsible for kringle 1-3 region protein generation.

The present invention also includes methods for the detection of deglycosylated kringle 1-3 region proteins in body fluids and tissues for the purpose of determining the efficacy of treatment and for the prognosis and diagnosis of angiogenesis associated diseases such as cancer. In particular, provided herein are methods of using antibodies that are specific for deglycosylated kringle 1-3 region proteins over circulating plasminogen. These methods provide a means to detect and distinguish deglycosylated kringle 1-3 region proteins from glycosylated kringle 1-3 region proteins and glycosylated plasminogen. The present invention also includes the detection of deglycosylated kringle 1-3 region protein binding sites and receptors in cells and tissues.

Kits for detection and measurement of deglycosylated kringle 1-3 region proteins, and the receptors therefor, are contemplated as part of the present invention. Antisera that possess the highest titer and specificity and can detect deglycosylated kringle 1-3 region proteins in extracts of plasma, urine, tissues, and in cell culture media are further examined to establish easy to use kits for rapid, reliable, sensitive, and specific measurement and localization of deglycosylated kringle 1-3 region proteins. These assay kits include but are not limited to the following techniques; competitive and non-competitive assays, radioimmunoassay, bioluminescence and chemiluminescence assays, fluorometric assays, sandwich assays, immunoradiometric assays, dot blots, enzyme linked assays including ELISA, antibody coated strips or dipsticks for rapid monitoring of urine or blood, and immunocytochemistry. For each kit the range, sensitivity, precision, reliability, specificity and reproducibility of the assay are established. Intra-assay and inter-assay variation is established at 20%, 50% and 80% points on the standard curves of displacement or activity.

The present invention also includes methods of treating or preventing angiogenic diseases and processes including, but not limited to, arthritis and tumors by stimulating the production of deglycosylated kringle 1-3 region proteins, and/or by administering substantially purified deglycosylated kringle 1-3 region proteins, nucleotides encoding deglycosylated kringle 1-3 region proteins, or deglycosylated kringle 1-3 region protein agonists or antagonists, and/or deglycosylated kringle 1-3 region protein antisera or antisera directed against deglycosylated kringle 1-3 region protein antisera to a patient. These angiostatin deglycosylated kringle 1-3 region proteins, deglycosylated kringle 1-3 region protein antisera, deglycosylated kringle 1-3 region protein receptor agonists or antagonists, or combinations thereof, are combined with pharmaceutically acceptable excipients, and optionally a sustained-release matrix, such as biodegradable polymers, to form therapeutic compositions. Additional treatment methods include administration of deglycosylated kringle 1-3 proteins, deglycosylated kringle 1-3 region protein analogs, deglycosylated kringle 1-3 region protein antisera, or deglycosylated kringle 1-3 region protein receptor agonists and antagonists linked to cytotoxic agents.

In one aspect of the present invention, a method of inhibiting angiogenesis in an individual comprises, increasing in the individual an in vivo concentration of a deglycosylated fragment of a kringle 1-3 region of a plasminogen protein relative to the in vivo concentrations of a glycosylated fragment of a kringle 1-3 region of a plasminogen protein and wherein the deglycosylated fragment of the kringle 1-3 region protein has antiangiogenic activity in vivo. The in vivo concentration of the deglycosylated fragment can be increased in any bodily fluid or tissue, but is preferably increased in the serum. In a further embodiment, a deglycosylated kringle 1-3 region protein is administered in a treatment effective amount to an individual in need of such treatment. In another embodiment, a gene encoding a deglycosylated fragment of a kringle 1-3 region of a plasminogen is administered to an individual using the gene therapy methods discussed in more detail below. Preferably the gene contains an amino acid substitution that prevents glycosylation during post-translational modification of the fragment of the kringle 1-3 region, and more preferably the substitution is at an amino acid corresponding to amino acid Asn-289 of human plasminogen.

A deglycosylated kringle 1-3 region protein is effective in treating diseases or processes that are mediated by, or involve, angiogenesis. The present invention includes the method of treating an angiogenesis mediated disease with an effective amount of a deglycosylated kringle 1-3 region protein, or combinations of deglycosylated kringle 1-3 region proteins that collectively possess antiangiogenic activity, or deglycosylated kringle 1-3 region protein agonists and antagonists. The angiogenesis mediated diseases include, but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. Deglycosylated kringle 1-3 region protein is useful in the treatment of disease of excessive or abnormal stimulation of endothelial cells. These diseases include, but are not limited to, intestinal adhesions, Crohn's disease, atherosclerosis, scleroderma, and hypertrophic scars, i.e., keloids. Deglycosylated kringle 1-3 region proteins can be used as a birth control agent by preventing vascularization required for embryo implantation. Deglycosylated kringle 1-3 region proteins are also useful in the treatment of diseases that have angiogenesis as a pathologic consequence such as cat scratch disease (Rochele minalia quintosa) and ulcers (*Helicobacter pylori*).

Deglycosylated kringle 1-3 region proteins may be used in combination with other compositions and procedures for the treatment of diseases. For example, a tumor may be treated conventionally with surgery, radiation or chemotherapy combined with deglycosylated kringle 1-3 region proteins and then deglycosylated kringle 1-3 region proteins may be subsequently administered to the patient to extend the dormancy of micrometastases and to stabilize and inhibit the growth of any residual primary tumor.

In addition to methods of administering deglycosylated kringle 1-3 region proteins, included in the present invention are methods of passive antibody therapy. In one embodiment, deglycosylated kringle 1-3 region protein antibodies block the action of excess endogenous deglycosylated kringle 1-3 region proteins. Specifically blocking the action of excess endogenous deglycosylated kringle 1-3 region proteins (versus endogenous glycosylated kringle 1-3 region proteins) is important considering the novel teaching herein that deglycosylated kringle 1-3 region proteins are more antiangiogenic than glycosylated kringle 1-3 region proteins. This treatment provides an improved method of modulating angiogenic-dependent processes such as reproduction, development, and wound healing and tissue repair and treating abnormal ovulation, menstruation and placentation, and vasculogenesis. This method also provides a useful tool to examine the effects of deglycosylated kringle 1-3 region protein removal on metastatic processes.

In another embodiment, antisera directed to the Fab regions of deglycosylated kringle 1-3 region protein antibodies can be administered to block the ability of endogenous deglycosylated kringle 1-3 region protein antisera to bind deglycosylated kringle 1-3 region proteins. The net effect of this treatment is to facilitate the ability of endogenous circulating deglycosylated kringle 1-3 region protein to reach target cells, thereby decreasing the spread of metastases.

The deglycosylated kringle 1-3 region proteins and antibodies thereto described above can be provided as isolated and substantially purified proteins and protein fragments in pharmaceutically acceptable formulations using formulation methods known to those of ordinary skill in the art. The deglycosylated kringle 1-3 region proteins and antibodies thereto described above may be a solid, liquid or aerosol. Examples of solid therapeutic compositions include pills, creams, and implantable dosage units. The pills may be administered orally and the therapeutic creams may be administered topically. The implantable dosage units may be administered locally, for example at a tumor site, or may be implanted for systemic release of the therapeutic angiogenesis-modulating composition, for example subcutaneously. Examples of liquid compositions include formulations adapted for injection subcutaneously, intravenously, intraarterially, and formulations for topical and intraocular administration. Examples of aerosol formulations include inhaler formulations for administration to the lungs. In general however, the formulations may be administered by any route, including but not limited to, the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route.

In addition, the deglycosylated kringle 1-3 region proteins and antibodies thereto may be incorporated into biodegradable polymers allowing for sustained release of the compound, the polymers being implanted in the vicinity of where drug delivery is desired, for example, at the site of a tumor or implanted so that the deglycosylated kringle 1-3 region protein or antibody is slowly released systemically. The biodegradable polymers and their use are described, for example, in detail in Brem et al., "Interstitial chemotherapy with drug polymer implants for the treatment of recurrent gliomas" *J. Neurosurg.* 74:441–446 (1991). Osmotic minipumps may also be used to provide controlled delivery of high concentrations of deglycosylated kringle 1-3 region proteins and antibodies thereto through cannulae to the site of interest, such as directly into a metastatic growth or into the vascular supply to that tumor.

The dosage of the deglycosylated kringle 1-3 region proteins and antibodies of the present invention will depend on the disease state or condition being treated and other clinical factors such as weight and condition of the human or animal and the route of administration of the compound. For treating humans or animals, between approximately 0.5 mg/kilogram per day to 500 mg/kilogram per day of the deglycosylated kringle 1-3 region protein can be administered. Depending upon the half-life of the deglycosylated kringle 1-3 region protein in the particular animal or human, it can be administered between several times per day to once a week. It is to be understood that the present invention has application for both human and veterinary use. The methods of the present invention contemplate single as well as multiple administrations, given either simultaneously or over an extended period of time.

The deglycosylated kringle 1-3 region protein formulations may conveniently be presented in unit dosage form and may be prepared by conventional pharmaceutical techniques. Such techniques include the step of bringing into association the active ingredient and the pharmaceutical carrier(s) or excipient(s). Suitable pharmaceutical carriers and excipients are known to those skilled in the art, however, an example of a suitable pharmaceutical excipient is water. In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules or vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, of the administered ingredient. It should be understood that in addition to the ingredients, particularly mentioned above, the formulations of the present invention may include other agents conventional in the art having regard to the type of formulation in question. Optionally, cytotoxic agents may be incorporated or otherwise combined with deglycosylated kringle 1-3 region proteins, or biologically functional protein fragments thereof, to provide dual therapy to the patient.

The present invention also encompasses gene therapy whereby the gene encoding a deglycosylated kringle 1-3 region protein is regulated in a patient. Various methods of transferring or delivering DNA to cells for expression of the gene product, otherwise referred to as gene therapy, are disclosed in "Gene Transfer into Mammalian Somatic Cells in vivo", N. Yang, *Crit. Rev. Biotechn.* 12(4):335–356 (1992). Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating medical problems with gene therapy include therapeutic strategies such as replacing a defective gene with a functional gene or adding a functional gene to augment a slightly functional gene. The genes inserted may treat a disease or condition or make the tissue or organ more susceptible to a treatment regimen. With regard to the present invention, a gene for a deglycosylated kringle 1-3 region protein may be placed in a subset of cells, thus preventing the occurrence of angiogenesis in the transformed cells.

Many protocols for the transfer of deglycosylated kringle 1-3 region protein DNA or deglycosylated kringle 1-3 region protein regulatory sequences are envisioned in this invention. Transfection of promoter sequences, other than one normally found specifically associated with a deglycosylated kringle 1-3 region protein, or other sequences that would increase production of deglycosylated kringle 1-3 region proteins are envisioned as methods of gene therapy. Such "genetic switches" could be used to activate a deglycosylated kringle 1-3 region protein (or the deglycosylated kringle 1-3 region protein receptor) in cells not normally expressing deglycosylated kringle 1-3 region protein (or the deglycosylated kringle 1-3 region protein receptor).

Gene transfer methods for gene therapy fall into three broad categories: (1) chemical (lipid-based carriers, or other non-viral vectors), (2) biological (virus-derived vector and receptor uptake), and (3) physical (electroporation, direct gene transfer and particle bombardment). Gene therapy methodologies can also be described by delivery site. Fundamental ways to deliver genes include ex vivo gene transfer, in vitro gene transfer, and in vivo gene transfer. In ex vivo gene transfer, cells are taken from the patient and grown in cell culture. The DNA is transfected into the cells, the transfected cells are expanded in number and then re-implanted in the patient. The present invention encompasses the removal of endothelial cells from a patient, transfection of DNA encoding a deglycosylated kringle 1-3 region protein, or regulatory sequence thereof, and re-introduction of the transfected endothelial cells into the patient. In in vitro gene transfer, transformed cells, such as endothelial cells, growing in culture are introduced into the patient. The transformed cells are not taken from the patient who will receive the gene therapy. In vivo gene transfer involves introducing the DNA into the cells of the patient when the cells are within the patient. Methods include using a noninfectious virus to introduce a gene into a patient or injecting naked DNA into a site in the patient whereby DNA is taken up by a percentage of cells in which the gene product protein is expressed. In the present invention, DNA encoding a deglycosylated kringle 1-3 region protein can be introduced into the endothelial cells lining the blood vessels, thereby inhibiting angiogenesis. In a preferred embodiment, the DNA encoding a deglycosylated kringle 1-3 region protein is introduced into endothelial cells lining the blood vessels in close proximity to a tumor.

Chemical methods of gene therapy may involve a lipid based compound, not necessarily a liposome, used to ferry the DNA across the cell membrane. Lipofectins or cytofectins, lipid-based positive ions that bind to negatively charged DNA, make a complex that can cross the cell membrane and provide the DNA into the interior of the cell. Liposome/DNA complexes may be directly injected intravenously into the patient. It is believed that the liposome/DNA complexes are concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA. Other DNA carrier systems include the asialoglycoprotein/polylysine conjugate system for carrying DNA to hepatocytes for in vivo gene transfer and DNA coupled to nuclear proteins in specifically engineered vesicle complexes that are carried directly into the nucleus.

Biological methods used in gene therapy techniques may involve receptor-based endocytosis, or receptor-based phagocytosis, which involve binding a specific ligand to a cell surface receptor and enveloping and transporting the ligand across the cell membrane. Specifically, a ligand/gene complex is created and injected into the blood stream. Target cells having a receptor for the ligand will specifically bind the ligand and transport the ligand-DNA complex into the cell. Additional biological methods employ viral vectors to insert genes into cells. For example, altered retrovirus vectors have been used in ex vivo methods to introduce genes into peripheral and tumor-infiltrating lymphocytes, hepatocytes, epidermal cells, myocytes, and other somatic cells. These altered cells are then introduced into the patient.

Viral vectors have also been used to insert genes into cells using in vivo protocols. To accomplish tissue-specific expression of foreign genes, cis-acting regulatory elements or promoters that are known to be tissue specific can be used. Alternatively, tissue-specific expression can be achieved using in situ delivery of DNA or viral vectors to specific anatomical sites in vivo. For example, gene transfer to blood vessels in vivo has been achieved by implanting in vitro transduced endothelial cells in chosen sites on arterial walls. Surrounding cells were infected by the virus and therefore also expressed the gene product. A viral vector can be delivered directly to the in vivo site, by a catheter for example, thus allowing only certain areas to be infected by the virus. In vivo gene transfer using retrovirus vectors has also been demonstrated in mammary tissue and hepatic tissue by injection of the altered virus into blood vessels leading to the organs.

Viral vectors that have been used for gene therapy protocols include, but are not limited to, retroviruses such as murine leukemia retroviruses, RNA viruses such as poliovirus or Sindbis virus, adenovirus, adeno-associated virus, herpes viruses, SV40, vaccinia and other DNA viruses. Replication-defective murine retroviral vectors are the most widely utilized gene transfer vectors. Fundamental advantages of retroviral vectors for gene transfer include efficient infection and gene expression in most cell types, precise single copy vector integration into target cell chromosomal DNA, and ease of manipulation of the retroviral genome. The adenovirus is capable of transducing novel genetic sequences into target cells in vivo. Adenoviral-based vectors express gene product proteins at high levels and have high efficiencies of infectivity, even with low titers of virus. Additionally, the virus is fully infective as a cell free virion so injection of expression cell lines is not necessary. Another potential advantage to adenoviral vectors is the ability to achieve long term expression of heterologous genes in vivo.

Mechanical methods of DNA delivery include direct injection of DNA, such as microinjection of DNA into germ or somatic cells, pneumatically delivered DNA-coated particles, such as the gold particles used in a "gene gun," inorganic chemical approaches such as calcium phosphate transfection and electroporation. It has been found that injecting plasmid DNA into muscle cells yields high percentage of the cells that are transfected and have sustained expression of marker genes. The DNA of the plasmid may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be re-injected periodically to maintain the gene product level without mutations occurring in the genomes of the recipient cells. Non-integration of exogenous DNAs may allow for the presence of several different exogenous DNA constructs within one cell with all of the constructs expressing various gene products.

Both particle-mediated gene transfer methods and electroporation can be used in in vitro systems, or with ex vivo or in vivo techniques to introduce DNA into cells, tissues or organs. With regard to particle-mediated gene transfer, a particle bombardment device, or "gene gun," is used that generates a motive force to accelerate DNA-coated high density particles (such as gold or tungsten). These particles penetrate the target organs, tissues or cells. Electroporation mediated gene transfer comprises the use of a brief electric impulse with a given field strength that is used to increase the permeability of a membrane in such a way that DNA molecules can penetrate into the cells.

The gene therapy protocol for transfecting DNA encoding deglycosylated kringle 1-3 region proteins into a patient may either be through integration of the deglycosylated kringle 1-3 region protein DNA into the genome of the cells, into minichromosomes or as a separate replicating or non-replicating DNA construct in the cytoplasm or nucleoplasm of the cell. Deglycosylated kringle 1-3 region protein expression may continue for a long-period of time or the DNA may be re-injected periodically to maintain a desired level of the deglycosylated kringle 1-3 region protein in serum or in a cell, tissue or organ.

This invention is further illustrated by the following examples, which are not to be construed in any way as imposing limitations upon the scope thereof. It is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Isolation of Glycosylated and Deglycosylated Kringle 1-3 Region Proteins

Human plasminogen was purified using affinity chromatography as described in Brockway, W. J. and Castellino, F. J., "Measurement and the binding of antifibrinolytic amino acids to various plasminogens" *Arch. Biochem. Biophys.* 151:194–199 (1972). One liter of human plasma (Children's Hospital blood bank) was applied to a 200 mL lys-Sepharose 4b (Pharmacia) column at a flow rate of 2–3 ml/minute. The column, previously equilibrated with 50 mM Tris pH 7.4 (Sigma) was then washed with 500 mL 50 mM tris/1M NaCl pH 7.4. Bound plasminogen was eluted with 200 mL 50 mM tris/200 mM ε-aminocaproic acid (εACA). The purity of this material was greater than 95% as assessed by SDS-PAGE. Human plasminogen was further fractionated into glycosylated plasminogen (plasminogen 1) and deglycosylated plasminogen (plasminogen 2) using lectin affinity chromatography. Human plasminogen (10 mg) was applied to a 5 mL conA HiTrap column (Pharmacia), equilibrated with 50 mM Tris pH 7.4/1 mM $MgCl_2$/1 MM $CaCl_2$. Plasminogen 2, lacking an N-linked carbohydrate, does not bind to this column. After washing the column with five column volumes of equilibration buffer, plasminogen I was eluted using a solution of 50 mM Tris pH 7.4/1 mM $MgCl_2$/1 mM $CaCl_2$. Protein concentration was determined spectrophotometrically as a wavelength of 280 nm using an A 0.1%/1 cm of 1.6 (computed from the protparam tool available at the ExPASy Molecular Biology World Wide Web (WWW) server at the Swiss Institute of Bioinformatics).

Plasminogen 1 and 2 were dialyzed against 20 mM Tris pH 7.6. Equal amounts of these glycoforms (as determined by A280 nm) were then digested with porcine pancreatic elastase (PPE) as described in O'Reilly, M. S. et al., "Angiostatin induces and sustains dormancy of human primary tumors in mice" *Nature Medicine* 2:689–692 (1996). Essentially, plasminogen was digested at 37° C. with 0.8 units of PPE (Calbiochem) per milligram of plasminogen. After five hours incubation, the reaction was quenched by applying the reaction mixture to a lys-Sepharose 4b column (10 mL), and eluting an approximately kringle 1-3 fragment of plasminogen and other lysine binding fragments, such as kringle 4, with 5 mL 200 mM εACA/50 mM Tris pH 7.4. The kringle 1-3 region protein was separated from kringle 4 and other smaller (<12 kDa) fragments using gel filtration on a Superdex200 HR 10/30 column (Pharmacia). The Superdex200 column was equilibrated with PBS. Kringle 1-3 region protein concentration was determined spectrophotometrically at a wavelength of 280 nm, using A 0.1%/1 cm value of 1.87 (computed from the protparam tool available at the ExPASy Molecular Biology World Wide Web (WWW) server at the Swiss Institute of Bioinformatics).

Bovine capillary endothelial cells were obtained as described previously in O'Reilly, M. S. et al. "Angiostatin: a novel angiogenesis inhibitor that mediates the suppression of metastases by a Lewis lung carcinoma" *Cell* 79:315–328 (1994) and were maintained in DMEM with 10% heat-inactivated BCS, antibiotics, and 3 ng/mL recombinant human bFGF (Scios Nova, Calif.). Cells were washed with PBS and dispersed in a 0.05% solution of trypsin. A cell suspension was made with DMEM/10% BCS/1% antibiotics and the concentration adjusted to 25,000 cells/ml. Cells were plated onto gelatinized 24-well culture plates (0.5 mL/well) and were incubated at 37° C. in 10% $CO_2$ for 24 hours. The media was replaced with 0.25 mL of DMEM/5% BCS/1% antibiotics, and the test sample applied. After 20 minutes incubation, media and bFGF were added to each well to obtain a final volume of 0.5 mL DMEM/5% BCS/1% antibiotics/1 ng/mL bFGF. After 72 hours, cells were dispersed in trypsin, resuspended in Hematell (Fisher scientific, PA) and counted by Coulter counter. Data from endothelial cell proliferation assays were plotted and $IC_{50}$ values determined using SigmaPlot. All data points were determined in triplicate from four separate preparations of kringle 1-3 region protein.

EXAMPLE 2

Figure 3:
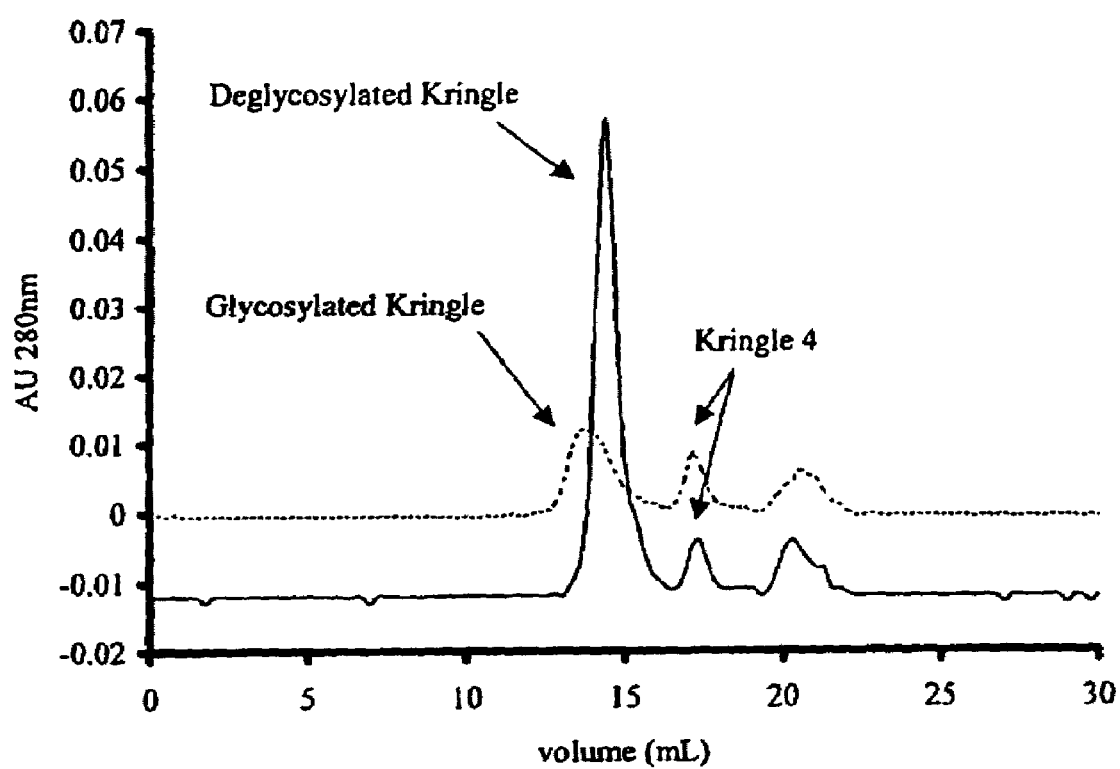
FIG. 3 shows the purification of glycosylated and deglycosylated kringle 1-3 region proteins using gel filtration chromatography.
Figure 4:
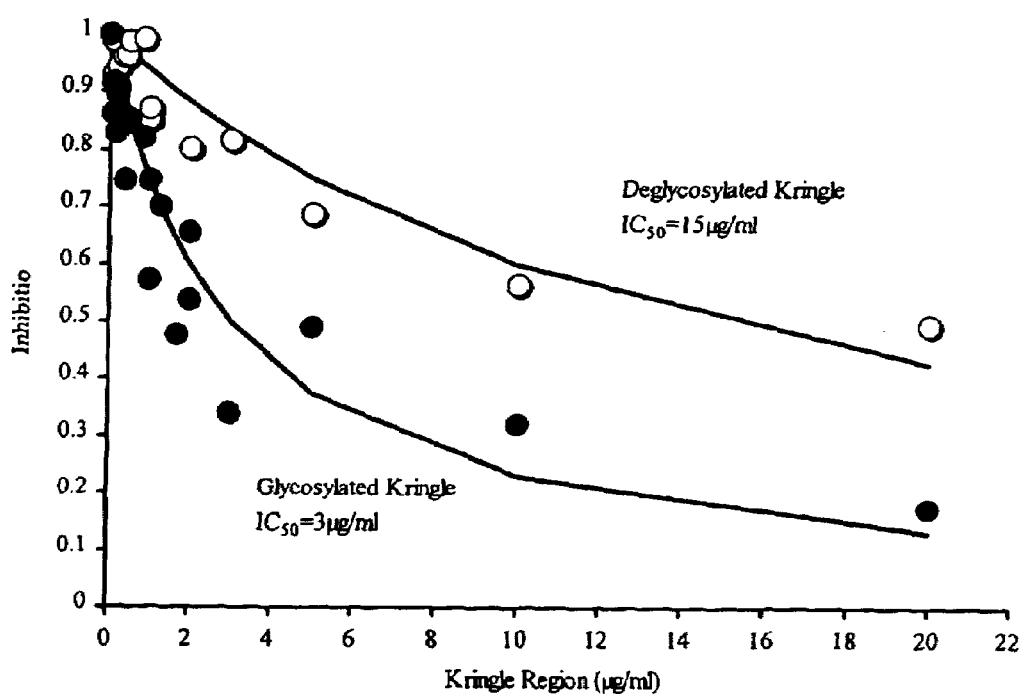
FIG. 4 shows the inhibition of endothelial cell proliferation by glycosylated and deglycosylated kringle 1-3 region proteins.

Deglycosylation of Plasminogen Results in an Increased Yield of Kringle 1-3 Region Proteins Equal amounts of plasminogen 1 and plasminogen 2 were digested with PPE, and the kringle 1-3 region proteins purified as described in Example 1 using a combination of affinity chromatography (lys-Sepharose) to purify kringle 1-3 region proteins and other lysine binding fragments of plasminogen, and gel filtration (Superdex200) to separate kringle 1-3 region proteins from kringle 4. FIG. 2 shows a typical chromatogram from the affinity column, demonstrating the reduced yield obtained when plasminogen 1 is used, as a substrate compared to plasminogen 2. FIG. 3 shows the chromatogram obtained from a typical gel filtration experiment as described in Example 1). It was noted that kringle 1-3 region protein from plasminogen I has a slightly lower retention time (13.77 minutes) than deglycosylated kringle 1-3 region protein (14.36 minutes), as would be expected from this glycosylated fragment. The yield of kringle 1-3 region proteins from plasminogen 2 was 4–5 fold higher than the yield of kringle 1-3 region proteins using plasminogen 1 as a substrate. Glycosylated kringle 1-3 region proteins migrated at approximately 40 kDa and deglycosylated kringle 1-3 region proteins migrated at 38 kDa on SDS-PAGE (data not shown). Edman degradation amino-terminal sequence analysis of both kringle 1-3 region protein glycoforms, gave identical sequence starting at Arg87, 16 residues amino-terminal to the cysteine residue that marks the beginning of kringle 1.

Therefore, it was determined that the presence of N-linked carbohydrate on Asn-289 modulates the generation of kringle 1-3 region proteins from human plasminogen. The presence of carbohydrate results in a 4–5-fold lower yield of kringle 1-3 region protein when PPE is used to cleave kringle 1-3 region proteins out of plasminogen. It was also determined that fractionation of kringle 1-3 region proteins generated from material containing glycosylated plasminogen (plasminogen 1) and deglycosylated plasminogen (plasminogen 2) in the ratio 40:60 using lectin affinity chromatography resulted in only 5–10% of glycosylated kringle 1-3 region proteins (data not shown). This data further indicated that N-linked carbohydrate is a negative modulator of kringle 1-3 region protein generation. Both kringle 1-3 region glycoforms had identical N-terminal sequence, indicating that the carbohydrate did not interfere with the site of proteolytic cleavage.

Although glycosylated kringle 1-3 region proteins were less efficiently generated and less efficient as an inhibitor or angiogenesis, it may be that kringle 1-3 region proteins containing N-linked carbohydrate, will have a longer clearance time than deglycosylated kringle 1-3 region proteins. This may be a mechanism to ensure persistence of anti-endothelial activity systemically, albeit at a reduced level.

EXAMPLE 3

Deglycosylated Kringle 1-3 Region Proteins Have Increased Antiangiogenic Activity as Compared to Glycosylated Kringle 1-3 Region Proteins Both kringle 1-3 region protein glycoforms were assayed for their ability to inhibit the proliferation of bovine endothelial cells as described in Example 1. Both kringle 1-3 region protein glycoforms inhibited endothelial cell proliferation. However, glycosylated kringle 1-3 region protein, which contains an N-linked carbohydrate, has a measured $IC_{50}$ value of approximately 13 μg/mL, whereas deglycosylated kringle 1-3 region protein, the glycoform, lacking an N-linked carbohydrate, has a measured $IC_{50}$ value of approximately 2.4 μg/nL. Thus, deglycosylated kringle 1-3 region protein appears to be a much more efficient inhibitor of endothelial cell proliferation, and in particular was 4–5 fold more efficient as an inhibitor of endothelial cell proliferation.

All patents, publications and abstracts cited above are hereby incorporated by reference. It should be understood that the foregoing relates only to preferred embodiments of the present invention, and that numerous modifications or alterations may be made therein without departing from the spirit and the scope of the invention as set forth in the appended claims.

---

We claim:

1. A composition comprising a pharmaceutically acceptable carrier and a protein consisting of a deglycosylated kringle 1-3 region fragment of a plasminogen protein, wherein the deglycosylated kringle 1-3 region fragment lacks one or two carbohydrate moieties found in naturally glycosylated forms of the fragment, wherein the deglycosylated kringle 1-3 region fragment has antiangiogenic activity, and wherein the deglycosylated kringle 1-3 region fragment and a glycosylated form of the fragment are at a ratio of 100:0.

2. The composition of claim 1, wherein the deglycosylated kringle 1-3 region fragment lacks a bisialylated-biantennary glycan.

3. The composition of claim 1, wherein the deglycosylated kringle 1-3 region fragment lacks an N-linked carbohydrate moiety.

4. The composition of claim 1, wherein the deglycosylated kringle 1-3 region fragment lacks a carbohydrate chain at an amino acid position corresponding to an N-glycosylation site of human plasminogen.

5. The composition of claim 1, wherein the deglycosylated kringle 1-3 region fragment begins at approximately amino acid 87 of human plasminogen.

6. The composition of clam 1, wherein the deglycosylated kringle 1-3 region fragment amino acid sequence is shown in SEQ ID NO:2.

7. The composition of claim 1, wherein the deglycosylated kringle 1-3 region fragment is produced recombinantly.

8. The composition of claim 1, wherein the deglycosylated kringle 1-3 region fragment has an amino acid substitution at amino acid position corresponding to the N-glycosylation site of human plasminogen.

9. The composition of claim 1, wherein the deglycosylated kringle 1-3 region fragment has antiangiogenic activity in vitro.

10. The composition of claim 1, wherein the deglycosylated kringle 1-3 region fragment has antiangiogenic activity in vivo.

11. A deglycosylated kringle 1-3 region fragment of a plasminogen protein, wherein the deglycosylated kringle 1-3 region fragment amino acid sequence is shown in SEQ ID NO:2.

12. The deglycosylated kringle 1-3 region fragment of claim 11, wherein the deglycosylated kringle 1-3 region fragment is produced recombinantly.

13. The deglycosylated kringle 1-3 region fragment of claim 11, wherein the deglycosylated kringle 1-3 region fragment has antiangiogenic activity in vitro.

14. The deglycosylated kringle 1-3 region fragment of claim 11, wherein the deglycosylated kringle 1-3 region fragment has antiangiogenic activity in vivo.

15. A composition comprising a pharmaceutically acceptable carrier and a protein consisting of a deglycosylated kringle 1-3 region fragment of a plasminogen protein wherein the deglycosylated kringle 1-3 region fragment lacks one or more carbohydrate moieties linked to naturally glycosylated forms of the fragment, wherein the deglycosylated kringle 1-3 region fragment has antiangiogenic activity, and wherein the deglycosylated kringle 1-3 region fragment amino acid sequence is shown in SEQ ID NO:2.

16. The composition of claim 15, wherein the deglycosylated kringle 1-3 region fragment is produced recombinantly.

17. The composition of claim 15, wherein the deglycosylated kringle 1-3 region fragment has antiangiogenic activity in vitro.

18. The composition of claim 15, wherein the deglycosylated kringle 1-3 region fragment has antiangiogenic activity in vivo.

19. The composition of claim 15, further comprising a protein consisting of a naturally glycosylated kringle 1-3 region fragment of a plasminogen protein.

20. The composition of claim 19, wherein the amount of the naturally glycosylated kringle 1-3 region fragment present in the composition is smaller than the amount of the deglycosylated kringle 1-3 region fragment present in the composition.

* * * * *

SEQUENCE LISTING

```
<160> NUMBER OF SEQ ID NOS: 2

<210> SEQ ID NO 1
<211> LENGTH: 780
<212> TYPE: DNA
<213> ORGANISM: Homo sapiens
<220> FEATURE:
<221> NAME/KEY: CDS
<222> LOCATION: (1)..(780)

<400> SEQUENCE: 1 gtg tat ctc tca gag tgc aag act ggg aat gga aag aat tac aga ggg      48
Val Tyr Leu Ser Glu Cys Lys Thr Gly Asn Gly Lys Asn Tyr Arg Gly
1               5                  10                  15 acg atg tcc aaa aca aaa aat ggc atc acc tgt caa aaa tgg agt tcc      96
Thr Met Ser Lys Thr Lys Asn Gly Ile Thr Cys Gln Lys Trp Ser Ser
                20                  25                  30 act tct ccc cac aga cct aga ttc tca cct gct aca cac ccc tca gag     144
Thr Ser Pro His Arg Pro Arg Phe Ser Pro Ala Thr His Pro Ser Glu
            35                  40                  45 gga ctg gag gag aac tac tgc agg aat cca gac aac gat ccg cag ggg     192
Gly Leu Glu Glu Asn Tyr Cys Arg Asn Pro Asp Asn Asp Pro Gln Gly
        50                  55                  60 ccc tgg tgc tat act act gat cca gaa aag aga tat gac tac tgc gac     240
Pro Trp Cys Tyr Thr Thr Asp Pro Glu Lys Arg Tyr Asp Tyr Cys Asp
65                  70                  75                  80 att ctt gag tgt gaa gag gaa tgt atg cat tgc agt gga gaa aac tat     288
Ile Leu Glu Cys Glu Glu Glu Cys Met His Cys Ser Gly Glu Asn Tyr
                85                  90                  95 gac ggc aaa att tcc aag acc atg tct gga ctg gaa tgc cag gcc tgg     336
Asp Gly Lys Ile Ser Lys Thr Met Ser Gly Leu Glu Cys Gln Ala Trp
                100                 105                 110 gac tct cag agc cca cac gct cat gga tac att cct tcc aaa ttt cca     384
Asp Ser Gln Ser Pro His Ala His Gly Tyr Ile Pro Ser Lys Phe Pro
            115                 120                 125 aac aag aac ctg aag aag aat tac tgt cgt aac ccc gat agg gag ctg     432
Asn Lys Asn Leu Lys Lys Asn Tyr Cys Arg Asn Pro Asp Arg Glu Leu
        130                 135                 140 cgg cct tgg tgt ttc acc acc gac ccc aac aag cgc tgg gaa ctt tgt     480
Arg Pro Trp Cys Phe Thr Thr Asp Pro Asn Lys Arg Trp Glu Leu Cys
145                 150                 155                 160 gac atc ccc cgc tgc aca aca cct cca cca tct tct ggt ccc acc tac     528
Asp Ile Pro Arg Cys Thr Thr Pro Pro Pro Ser Ser Gly Pro Thr Tyr
                165                 170                 175
```

```
cag tgt ctg aag gga aca ggt gaa aac tat cgc ggg aat gtg gct gtt      576
Gln Cys Leu Lys Gly Thr Gly Glu Asn Tyr Arg Gly Asn Val Ala Val
            180                 185                 190 acc gtg tcc ggg cac acc tgt cag cac tgg agt gca cag acc cct cac      624
Thr Val Ser Gly His Thr Cys Gln His Trp Ser Ala Gln Thr Pro His
        195                 200                 205 aca cat gaa agg aca cca gaa aac ttc ccc tgc aaa aat ttg gat gaa      672
Thr His Glu Arg Thr Pro Glu Asn Phe Pro Cys Lys Asn Leu Asp Glu
    210                 215                 220 aac tac tgc cgc aat cct gac gga aaa agg gcc cca tgg tgc cat aca      720
Asn Tyr Cys Arg Asn Pro Asp Gly Lys Arg Ala Pro Trp Cys His Thr
225                 230                 235                 240 acc aac agc caa gtg cgg tgg gag tac tgt aag ata ccg tcc tgt gac      768
Thr Asn Ser Gln Val Arg Trp Glu Tyr Cys Lys Ile Pro Ser Cys Asp
                245                 250                 255 tcc tcc cca gta                                                      780
Ser Ser Pro Val
            260

<210> SEQ ID NO 2
<211> LENGTH: 260
<212> TYPE: PRT
<213> ORGANISM: Homo sapiens

<400> SEQUENCE: 2

Val Tyr Leu Ser Glu Cys Lys Thr Gly Asn Gly Lys Asn Tyr Arg Gly
1               5                   10                  15

Thr Met Ser Lys Thr Lys Asn Gly Ile Thr Cys Gln Lys Trp Ser Ser
            20                  25                  30

Thr Ser Pro His Arg Pro Arg Phe Ser Pro Ala Thr His Pro Ser Glu
        35                  40                  45

Gly Leu Glu Glu Asn Tyr Cys Arg Asn Pro Asp Asn Asp Pro Gln Gly
    50                  55                  60

Pro Trp Cys Tyr Thr Thr Asp Pro Glu Lys Arg Tyr Asp Tyr Cys Asp
65                  70                  75                  80

Ile Leu Glu Cys Glu Glu Cys Met His Cys Ser Gly Glu Asn Tyr
                85                  90                  95

Asp Gly Lys Ile Ser Lys Thr Met Ser Gly Leu Glu Cys Gln Ala Trp
                100                 105                 110

Asp Ser Gln Ser Pro His Ala His Gly Tyr Ile Pro Ser Lys Phe Pro
            115                 120                 125

Asn Lys Asn Leu Lys Lys Asn Tyr Cys Arg Asn Pro Asp Arg Glu Leu
        130                 135                 140

Arg Pro Trp Cys Phe Thr Thr Asp Pro Asn Lys Arg Trp Glu Leu Cys
145                 150                 155                 160

Asp Ile Pro Arg Cys Thr Thr Pro Pro Ser Ser Gly Pro Thr Tyr
                165                 170                 175

Gln Cys Leu Lys Gly Thr Gly Glu Asn Tyr Arg Gly Asn Val Ala Val
            180                 185                 190

Thr Val Ser Gly His Thr Cys Gln His Trp Ser Ala Gln Thr Pro His
        195                 200                 205

Thr His Glu Arg Thr Pro Glu Asn Phe Pro Cys Lys Asn Leu Asp Glu
    210                 215                 220
```

```
-continued

Asn Tyr Cys Arg Asn Pro Asp Gly Lys Arg Ala Pro Trp Cys His Thr
225                 230                 235                 240

Thr Asn Ser Gln Val Arg Trp Glu Tyr Cys Lys Ile Pro Ser Cys Asp
                245                 250                 255

Ser Ser Pro Val
            260
```